United States Patent [19]

Swindle

[11] Patent Number: 5,213,093
[45] Date of Patent: May 25, 1993

[54] ENDOSCOPE WITH NON-CIRCULAR PROBE AND METHOD OF MAKING SAME

[75] Inventor: Carl A. Swindle, Irvine, Calif.

[73] Assignee: Applied Vascular Devices, Inc., Laguna Hills, Calif.

[21] Appl. No.: 706,804

[22] Filed: May 29, 1991

[51] Int. Cl.⁵ .............................................. A61B 1/00
[52] U.S. Cl. ........................................... 128/4; 128/6
[58] Field of Search ....................................... 128/4, 6

[56] References Cited

U.S. PATENT DOCUMENTS

| | | | |
|---|---|---|---|
| 4,690,175 | 9/1987 | Ouchi | 128/4 |
| 4,834,518 | 5/1989 | Barber | 128/4 |
| 4,841,949 | 6/1989 | Shimizu et al. | 128/4 |
| 4,972,828 | 11/1990 | Ito | 128/4 |
| 4,991,565 | 2/1991 | Takahashi et al. | 128/4 |

FOREIGN PATENT DOCUMENTS 2503646 8/1976 Fed. Rep. of Germany .......... 128/4

OTHER PUBLICATIONS

Drawing of Model MR-6 by American Cystoscope Makers Inc.

*Primary Examiner*—John G. Weiss
*Attorney, Agent, or Firm*—Richard L. Myers

[57] ABSTRACT

An endoscope having a proximal end and a distal end includes a housing disposed at the proximal end and a probe attached to the housing and extending along an axis to the distal end of the endoscope. The probe has a wall with an outer surface and an inner surface which defines a lumen extending along an axis from the housing to the distal end of the endoscope. At least a portion of the wall includes an outer surface with a tapered shape in axial cross-section and a non-circular shape in radial cross-section.

24 Claims, 3 Drawing Sheets

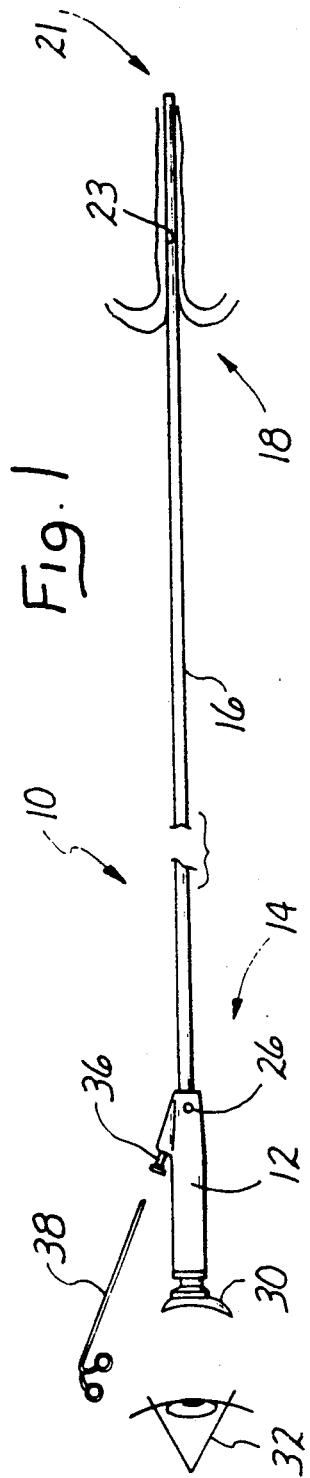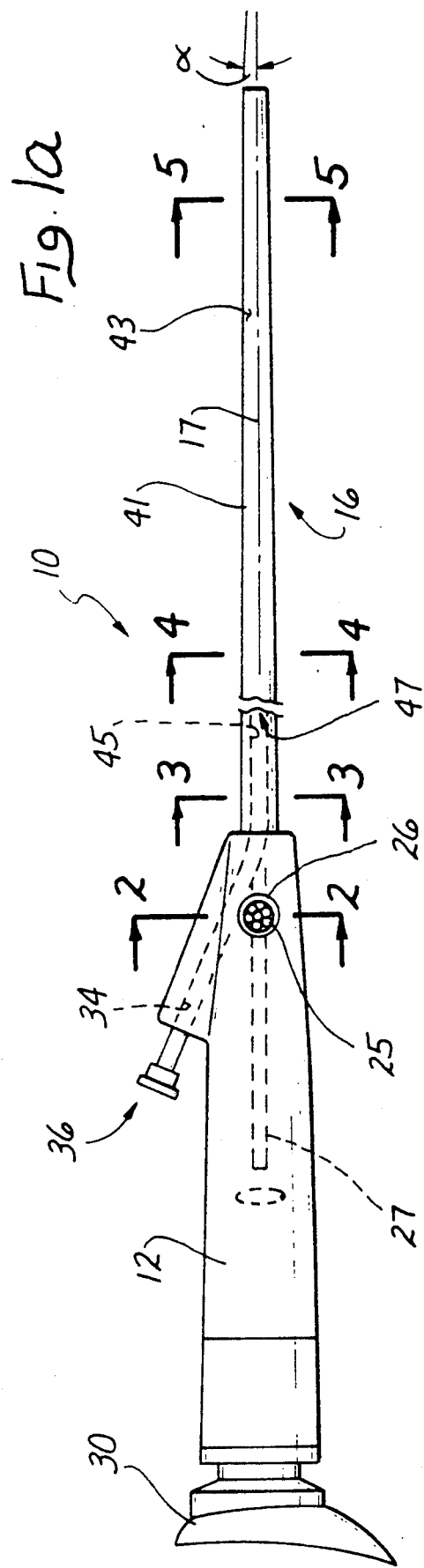

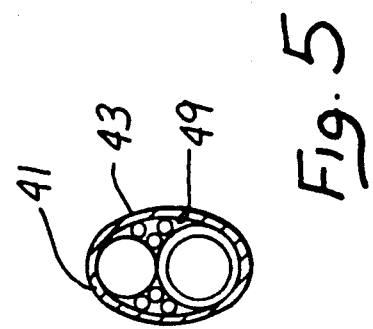
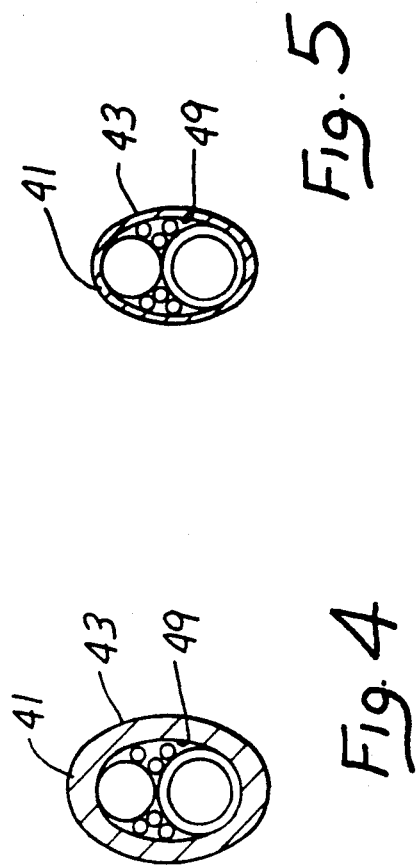
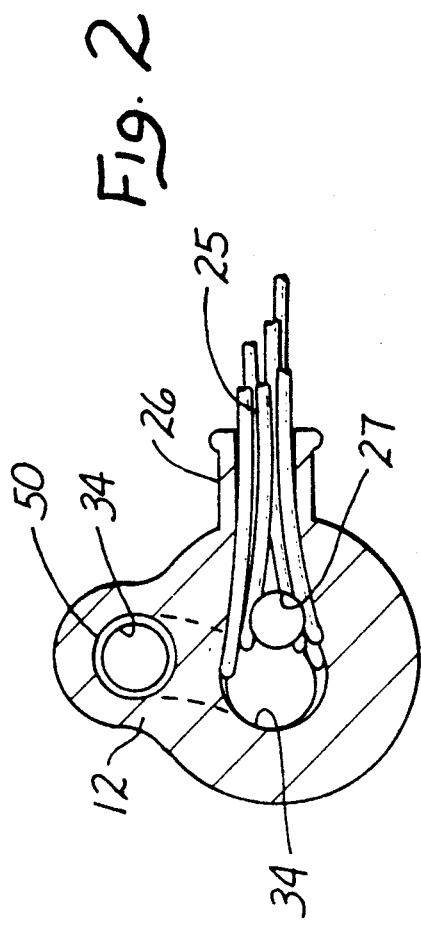
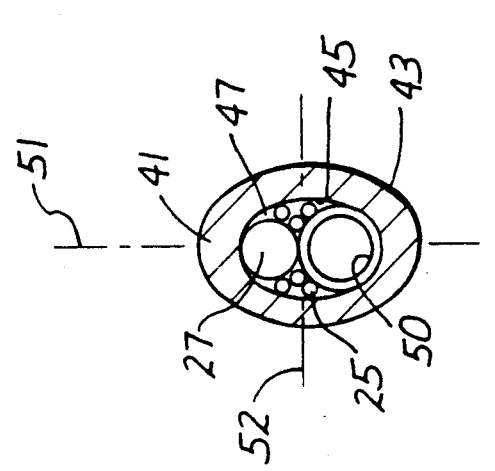

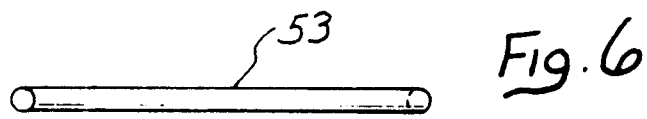
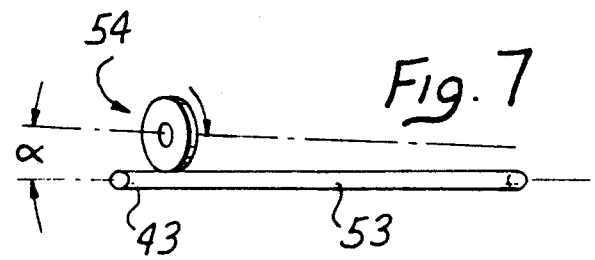
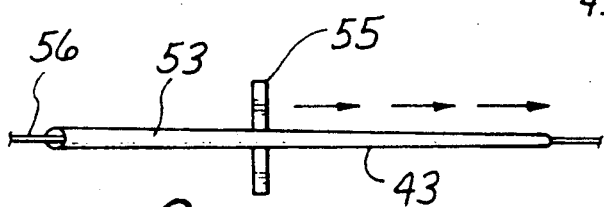
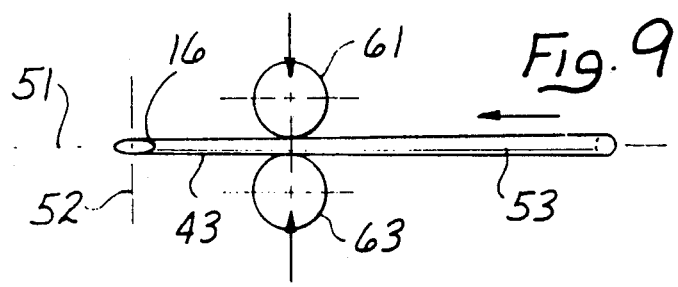
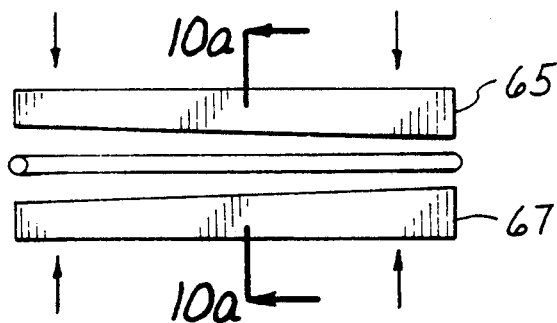
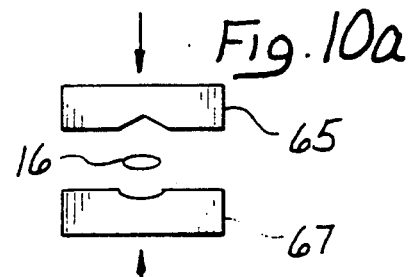
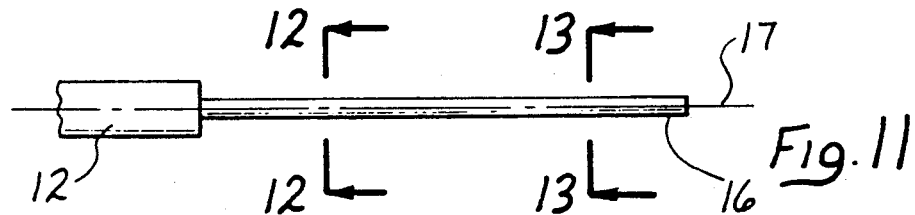
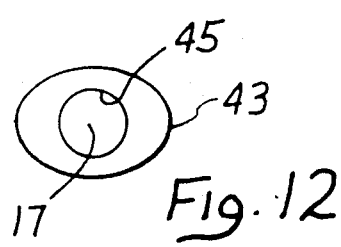
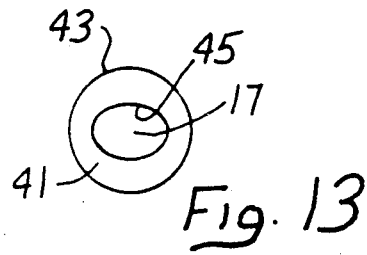

ENDOSCOPE WITH NON-CIRCULAR PROBE AND METHOD OF MAKING SAME

BACKGROUND OF THE INVENTION

1. Field of the Invention

This invention relates generally to endoscopes which provide for visualization of body cavities, openings, and conduits for surgical, diagnostic and therapeutic procedures.

2. Background of the Invention

An endoscope (sometimes referred to a "scope") is a device which is used to visualize body cavities, openings and conduits. This visualization is accomplished through light fibers which conduct light to the site of interest, and image fibers which return light images from the site being visualized. Typically endoscopes also include a working channel which permits the user to insert instruments which accomplish various operative functions, such as grasping, cutting and suturing, at the site being visualized. With these two purposes, visualization and operation, endoscopes are sometimes specifically configured to access a particular site and to perform a specific operative function at that site. These specialized scopes are sometimes referred to as cytoscopes, ureteroscopes, arthrascopes, laparoscopes, resectoscopes and the like.

An endoscope typically includes a housing which receives the fiberoptics and the surgical instruments from a location exterior of the patient, and a long narrow probe which extends from the housing to the operative site of interest. This probe may have an external diameter such as seven French and a length such as thirteen inches. The probe may be rigid, flexible, or semi-rigid depending primarily on the need to manipulate the tip of the probe through a torturous path. It is the configuration of this probe that is particular interest to the present invention.

The probes of the past have typically been cylindrical in configuration with an outer surface, and an inner surface defining a central lumen. In order to minimize trauma to the patient, it has always been of interest to decrease the cross-sectional circumference of the outer surface. This requirement has been directly opposed to the need to increase the cross-sectional circumference of the inner surface in order to maximize the size of the central lumen.

In a typical endoscope, the probe lumen may have a diameter of 0.089 inches. Within this diameter the central lumen must provide for a working channel having an outside diameter such as 0.050 inches, and a bundle of image fibers having a diameter such as 0.021 inches. Incident light fibers are generally much smaller in diameter and can be positioned in any of the remaining space not occupied by the working channel or the image bundle.

The conflict between the need to reduce the circumference of the outer surface and the need to increase the circumference of the inner surface of the probe has driven the technology to require a very thin wall for the probe. However, since the probe has a significant length to diameter ratio, the thin wall has made the probes highly susceptible to breaking. When one realizes that these probes are subjected to both torque and bending stresses as they are inserted through torturous paths, this tendency to break simply cannot be tolerated.

In order to reduce this risk of breaking, stress relief has been provided in the form of larger diameter, thicker walled tubes which have been disposed over the proximal end of the thin walled probe. This has tended to relieve the principal point of stress where the probe enters the housing. In some cases, several sleeves have been provided each with a reduced diameter in the distal direction. Unfortunately, in this configuration the sleeves tend to form shoulders on the outer surface of the probe. These shoulders also define points of significant bending stress, and additionally create a tendency for the outer surface of the probe to snag on various objects along the insertion path.

SUMMARY OF THE INVENTION

These problems associated with the prior art are avoided by the present invention which provides for an optimal configuration for the probe lumen without increasing the circumference of the outer surface of the probe. Reduced wall thicknesses for the probe can now be tolerated by providing the probe with a tapered configuration so that there are substantially no points of bending stress along the probe.

These features are achieved in one aspect of the invention where the probe is provided with a wall which defines an interior lumen extending along an elongate axis from the housing to the distal end of the endoscope. At least a portion of the wall has an 15 outer surface with a tapered shape in axial cross-section and a non-circular shape in radial cross-section.

In another aspect of the invention, the endoscope includes a housing and a probe which includes axial wall portions extending from a proximal region to a distal region of the probe. The thickness and geometry of the wall in the wall portion is substantially constant in any particular radial cross-section, but varies in progressive radial cross-sections along the wall portion of the probe.

The invention also includes a method for making an endoscope having these preferred structural characteristics. The method includes steps for providing a probe with tubular walls having a substantially constant thickness, tapering the thickness of the walls along an axial portion of the probe, and providing the tubular walls with a shape which, in a particular plane perpendicular to the axis of the tube, has a non-circular configuration.

These and other features and advantages of the invention will be more apparent with a description of preferred embodiments and reference to the associated drawings.

DESCRIPTION OF THE DRAWINGS

FIG. 1 is a perspective view of an endoscope illustrated in an operative disposition and including one embodiment of a probe associated with the present invention;

FIG. 1a is a side elevation view of the endoscope of FIG. 1 illustrating a tapered configuration of the probe;

FIG. 2 is a radial cross-section view taken along lines 2—2 of FIG. 1a;

FIG. 3 is a radial cross-section view taken along lines 3—3 of FIG. 1a;

FIG. 4 is a radial cross-section view taken along lines 4—4 of FIG. 1a;

FIG. 5 is a radial cross-section view taken along lines 5—5 of FIG. 1a;

FIG. 6-11 illustrate various steps in a preferred method for manufacturing the endoscope of the present invention;

FIG. 6 is a side view of an integral piece of cylindrical tubing for the probe;

FIG. 7 is a schematic view of a step for grinding a taper into the cylindrical probe of FIG. 6;

FIG. 8 illustrates a step of drawing the tubing of FIG. 6 into a tapered configuration;

FIG. 9 illustrates a step for rolling the tubing of FIG. 6 into a non-circular cross-section;

FIG. 10 illustrates a step of cold forming the tubing of FIG. into a tapered configuration;

FIG. 10a is a cross-section view of the tool of FIG. 10 taken along lines 10a—10a of FIG. 10;

FIG. 11 illustrates a step of assembling the tapered probe and the housing of the endoscope;

FIG. 12 is a radial cross-section view taken along lines 12—12 of FIG. 11; and

FIG. 13 is a radial cross-section view taken along lines 13—13 of FIG. 11.

DESCRIPTION OF PREFERRED EMBODIMENTS

An endoscope is illustrated in FIG. 1 and designated generally by the reference numeral 10. A hand piece or housing 12 is disposed at a proximal end 14 of the endoscope, while a probe 16 extends along an axis 17 from the housing to a distal end 18 of the endoscope. The endoscope 10 is adapted to provide for visualization of an operative site 21 interiorly of a body cavity or passage 23. By way of example, the operative site of interest may be the prostate in which case the cavity or passage is the urethra.

To provide for this visualization, light is introduced through light fibers 25 which extend into a side opening 26 in the housing 12 and through the probe 16 to illuminate the operative site 21. A bundle of image fibers 27, best shown in FIG. 2, extends from the distal end 18 of the endoscope 10 back to the housing 12 where it is coupled to an eyepiece 30. Typically, the housing 12 is held by the hand of a user and his eye 32 views the illuminated operative site 21 through the eyepiece 30.

The endoscope 10 may include an operative or working channel 34 which extends from an access port 36 in the housing 12, through the probe 16 to the distal end 18. The working channel 34 enables a user to insert various surgical materials or instruments, such as a pair of graspers 38, for extension through the endoscope 10 to the operative site 21. At this location, the instruments can be manipulated for both diagnostic and therapeutic purposes. Such materials and instruments may include, for example, X-ray or ultrasonic contrast agents, pharmaceuticals, cutting elements, balloons, irrigation tubes, suction apparatus, and the like.

Although the housing 12 can be provided with various shapes and functions, the particular embodiment disclosed in applicant's co-pending application Ser. No. 573,880 is of particular advantage to the present invention.

The probe 16 can be attached to the housing 12 in any conventional manner. In general, the probe 16 has a tubular configuration and includes a wall 41 having an outer surface 43 and an inner surface 45. It is this inner surface 45 which defines a lumen 47 that extends the entire length of the probe 16.

The probe 16 is relatively long in order to provide access to distant locations within the body. On the other hand, the probe 16 is very thin in order to facilitate its passage through narrow passages 23 such as the urethra. As a consequence, the probe 16 may have a relatively large aspect ratio (a length to average outside diameter ratio) such as 350.

As the endoscope 10 is twisted and manipulated to the operative site 21, it undergoes significant stresses which tend to bend the probe 16. In the past, the wall 41 has had a cylindrical configuration with a constant wall thickness. This configuration tends to focus the bending stresses at a point where the probe 16 enters the housing 12. Some stress relief has been provided at this location but that has merely tended to move the point of maximum stress toward the distal end 18 of the endoscope 10.

Stress relief is provided in accordance to the present invention by configuring the outer surface 43 with a taper which extends at an angle $\alpha$ relative to the axis 17. This taper can occur along any portion of the wall 41 between the housing 12 and the distal end 18. However, in a preferred embodiment, the outer surface 43 is tapered along the entire length of the probe 16.

While the outer surface 43 has a tapered configuration, the inner surface 45 maintains a fairly constant geometry for the lumen 47 through the entire probe 16. With the tapering outer surface 43, and a constant inner surface 45, it is apparent that the thickness of the wall 41 which forms the probe 16 will vary from a relatively thick wall 41 at the proximal end 14 of the probe 16 to a relatively thin wall 41 at the distal end 18 of the probe 16. These varying wall thickness are illustrated in the progressive drawings of FIGS. 3-5. With reference to these figures it is apparent that the lumen 47 remains constant along the length of the probe 16 while the outer surface 43 becomes increasingly smaller, with a reduced cross-sectional circumference, at progressive positions toward the distal end 18.

In the illustrated embodiment, the taper on the outer surface 43 of the probe 16 extends from the housing 12 to the distal end 18 of the endoscope 10. It will be apparent however, that this taper can be provided along any axial portion of the wall 41 and that it will provide appropriated stress relief within that wall portion. Where only a portion of the wall 41 is tapered, bending stresses will not focus at a single point, but rather will be distributed along the entire length of the tapered portion.

In a preferred embodiment the entire probe 16 is formed from a single piece of material, such as stainless steel, and tapered from the proximal end 14 to the distal end 18. This structural configuration offers the further advantage of a continuous and smooth outer surface 43 which is totally free of bumps or undulations.

The lumen 47 is adapted to receive a cylinder 50, which defines the working channel 34, as well as the bundle of image fibers 27 and the individual light fibers 25. It is the shape and relative size of the cylinder 50 and fibers 25 and 27 which are of particular interest to the present invention.

With reference to the cross-section view of FIG. 3, it will be apparent that the cylinder 50 and fibers 25, 27 are commonly provided with a circular outer diameter. However, the size of the cylinder 50 will be relatively large with an outer diameter such as 0.050 inches. The image fibers 27 form a bundle which may be only slightly smaller with a diameter such as 0.021 inches. By way of comparison, the individual light fibers 25 have a relatively small diameter such as 0.001.

In order to minimize the cross-sectional size of the probe 16, it is desirable that the lumen 47 be maintained at a minimum size or cross-sectional area. This is achieved in a preferred embodiment where the lumen 47 is provided with a non-circular shape. By way of example, this shape in a preferred embodiment is an oval having a major axis 51 and a minor axis 52.

Since the diameter of the cylinder 50 and the diameter of the image fibers 27 are much larger than the diameter of the light fibers 25, these two elements tend to dictate the size of the lumen 47. In accordance with the present invention, these two elements also dictate the shape of the lumen 47. Thus, in the illustrated embodiment, the cylinder 50 and image fibers 27 are disposed generally along the major axis 51 of the oval and the remaining space at the sides of the major axis 51 are filled with multiple light fibers 25. As illustrated in FIG. 3, the light fibers 25 can be disposed adjacent the cylinder 50 and image fibers 27, generally along the minor axis 52 of the oval. By thus constructing the lumen 47 with a non-circular configuration, the probe 16 is provided with a minimum size or cross-sectional area.

In a preferred embodiment, the oval lumen 47 has a length along the major axis 51 of 0.078 inches, and a width along the minor axis 52 of 0.062 inches. This shape is constant along the entire length of the probe 16. The outer surface 43 of the wall 41 is similar in shape to the surface 45 but is tapered along its entire thirteen inch length at an angle $\alpha$ equal to 0.044 degrees or 2.64 minutes. It follows, that if the walls 41 at the proximal end 14 of the probe 16 have a thickness of 0.016 inches, at the distal end 18 of the probe 16 the walls 41 will have a thickness of 0.007 inches.

Another feature associated with the present invention is an increased bending modulus which results from the non-circular cross section of the probe 16. When compared with a probe having the traditional circular configuration, the non-circular cross-section will provide at least one plane having a relatively higher bending modulus. In the case of an oval configuration, this particular plane includes the axis 17 of the probe 16 and the major axis 51 of the oval. In general, the bending moment along the major axis 5 is greater than the bending moment along the minor axis 52. Given this increased bending modulus, torque can be applied to the probe 16 along the particular plane without increasing the risk of bending.

A preferred method for manufacturing the endoscope 10 includes the step of providing a tube 53 for the probe 16. This tube 53 is illustrated in FIG. 6 and commonly has a constant wall thickness defined by an outer surface and an inner surface both of which are circular in radial cross-section. This cylindrical tube 53 can be seamless or welded and drawn with a specific outside diameter such as 0.109 and inside diameter such as 0.075 inches. In a preferred embodiment, the cylinder 53 is formed from a single piece of surgical stainless steel.

This tube 53 can be mounted on a grinder, such as the centerless grinder 54 illustrated in FIG. 7, and ground to form the tapered outer surface 43 previously discussed. On the centerless grinder 54, the tube 53 can be configured to form tapers, step diameters, grooves, or the like, to provide the outer surface 43 with any desired configuration. This formation of the outer surface 43 can also be accomplished by lathe turning or lathe grinding.

Alternatively, the taper can be formed by drawing the tube 53 through a die 55, as illustrated in FIG. 8, with progressive speeds so that the taper on the outer surface 43 is automatically formed. In such a drawing step, it may be desirable to provide a mandrel 56 in order to maintain a desired shape for the inner surface 45.

By thus altering the shape of the tube 53, the outer surface 43 can be provided with the tapered configuration while the inner surface 45 can be maintained with a cylindrical configuration. This will result in a wall thickness which is progressively reduced along the length of the tube 53. At this point in a preferred process, the walls of the tube 53 will be circular in cross-section; further steps must be taken to produce the desired oval configuration.

In FIG. 9, the tube 52 including the tapered outer surface 43, is forced through rollers which are loaded against opposite sides of the tube 52. For example, the tube 52 may be pushed between the compressing rollers 61 and 63, from right to left in FIG. 9. This results in a preferred embodiment of the probe 16 which includes the tapered outer surface 43, the progressively reduced thickness of the wall 41, and the desired oval configuration for the lumen 47.

The tube 53 can be tapered otherwise by placing it between dies 65 and 67 of a forming tool as illustrated in FIG. 10. These dies 65 and 67 may be longitudinally tapered to accommodate the taper on the tube 52 and provided with cross-sectional shapes such as the oval shape and "v" shape illustrated in the cross-section view of 10a. As the dies 65 and 67 are forced together, the tube 52 is compressed along the minor axis 52 to obtain its final form. Once the probe 16 has been formed, it can be joined to the housing 12 in a conventional manner, and the cylinder 50 and fibers 25, 27 can be loaded as illustrated in FIG. 3.

It will now be apparent that the inner surface 45 of the probe 16 can be provided with any shape by merely controlling the configuration of the mandrel 56, as illustrated in FIG. 8. Similarly, the outer surface 43 of the probe 16 can be provided generally with an shape by controlling the configuration of the dies 6 and 67 in FIGS. 10 and 10a.

In general, cross-sectional views taken at any two points along the probe 16, as illustrated in FIG. 11, will show an outer surface 43 having a first configuration in the first cross-section and a second configuration that is different from the first configuration in the second cross-section. With respect to the embodiment in FIG. 11, the outer surface 43 has an oval shape in FIG. 12 and a circular shape in FIG. 13. These two configurations of the outer surface 43 may be different in shape, as in the embodiment of FIG. 11, or they may be similar in shape but different in size, as in the embodiment shown in FIGS. 4 and 5.

These same configuration characteristics also apply to the inner surface 45 of the probe 16. For example, in FIG. 11, the inner surface 45 has a circular shape in FIG. 12 and an oval shape in FIG. 13. As noted with reference to FIG. 4, the shape of the inner surface 45 can be similar to the shape of the outer surface 43 in which case the thickness of the wall 41 does not vary in radial cross-section. Alternatively, as illustrated in FIG. 12, the inner surface 45 may not be dissimilar in shape to the outer surface 43, in which case the walls 41 vary in thickness radially of the axis 17.

Thus, the endoscope 10 can be provided with a probe 16 which includes stress relief along any axial portion of the probe 16 or along the entire length of the probe 16. This stress relief can be accomplished without increasing the outside circumference of the probe 16. In fact, by defining the lumen 47 with a non-circular shape, such as the shape of an oval, the overall size or cross-sectional area of the probe 16 can be reduced.

Although the preferred embodiment includes an outer surface 43 and an inner surface 45 which have shapes that are similar in cross-section, this is not required by the present invention. Thus, in any given cross-section through the probe 16, the inner surface 45 may have a shape, such as the shape of an oval, which is different from the shape of the outer surface 43, such as the shape of a circle. These shapes may also vary along the length of the probe 16 with consequential variations in the thickness of the wall 41. Wall thickness variations may occur not only axially as in the embodiment of FIG. 3, but also radially as in the embodiment of FIG. 11.

Although the invention has been described with reference to specific embodiments and methods, it will be apparent that the probe 16 can be otherwise embodied and manufactured. For this reason, the scope of the invention should be ascertained not merely with reference to the disclosed and illustrated embodiments, but rather with reference to the following claims.

I claim:

1. An endoscope having a proximal end and a distal end, comprising:
   a housing disposed at the proximal end of the endoscope;
   a probe attached to the housing and having a wall with an inner surface and an outer surface, the inner surface defining a lumen which extends through the probe;
   a first axial portion of the wall wherein the outer surface has a tapered shape in axial cross-section; and
   a second axial portion of the wall wherein the outer surface has a non-circular configuration in radial cross-section.

2. The endoscope recited in claim 1 wherein the lumen of the probe in radial cross-section is substantially constant in size and shape along the second axial portion of the wall.

3. The endoscope recited in claim 1 wherein the first axial portion of the wall is coextensive with the second axial portion of the wall.

4. The endoscope recited in claim 1 wherein the non-circular configuration is oval.

5. The endoscope recited in claim 1 wherein the first axial portion of the wall has an inner surface which in radial cross-section is similar in shape to the outer surface of the first axial portion of the wall.

6. The endoscope recited in claim 5 wherein the wall in the first axial wall portion has a substantially constant radial wall thickness.

7. The endoscope recited in claim 1 wherein the first axial portion of the wall has a proximal region and a distal region, and the wall in the first axial portion has a thickness which decreases from the proximal region to the distal region of the first axial portion.

8. An endoscope having a proximal end and a distal end comprising:
   a housing disposed at the proximal end of the endoscope and adapted to be grasped by the hand of the user;
   a probe attached to the housing and having a wall with an inner surface and an outer surface;
   the outer surface having a first configuration in a first radial cross-section of the probe, and a second configuration in a second radial cross-section of the probe;
   the inner surface has a third configuration in the first radial cross-section and a fourth configuration in the second radial cross-section; and
   the first configuration having a different shape than the third configuration.

9. The endoscope recited in claim 8 wherein the first configuration of the outer surface and the second configuration of the outer surface are similar in shape.

10. The endoscope recited in claim 8 wherein the third configuration in the first cross-section is similar in shape to the fourth configuration in the second cross-section.

11. The endoscope recited in claim 10 wherein one of the first configuration and the third configuration is circular in shape and the other of the first configuration and the third configuration is non-circular in shape.

12. The endoscope recited in claim 11 wherein the non-circular shape is oval.

13. The endoscope recited in claim 12 wherein the oval has a major axis and a minor axis, and the bending moment of the probe along the major axis is greater than the bending moment of the probe along the minor axis.

14. The endoscope recited in claim 10 wherein the third configuration is the same as the fourth configuration.

15. The endoscope recited in claim 12 wherein the first configuration has the oval shape.

16. An endoscope having a proximal end and a distal end, comprising:
   a housing disposed at the proximal end of the endoscope;
   a probe attached to the housing and having a wall with an inner surface and an outer surface, the inner surface of the wall defining a lumen which extends through the probe;
   the outer surface of the probe in a first radial cross-section having a first configuration and a first radial circumference;
   the outer surface in a second radial cross-section having a second configuration and a second radial circumference;
   the inner surface in the first radial cross-section having a third configuration and a third radial circumference;
   the inner surface in the second radial cross-section having a fourth configuration and a fourth radial circumference;
   the first configuration being non-circular in shape; and
   the second radial circumference being less than the first radial circumference.

17. The endoscope recited in claim 16 wherein the third configuration is similar in shape to the first configuration.

18. The endoscope recited in claim 16 wherein the third configuration is dissimilar in shape to the first configuration.

19. The endoscope recited in claim 16 wherein the second configuration is smaller in size and similar in shape to the first configuration.

20. An endoscope having a proximal end and a distal end, comprising:
   a housing disposed at the proximal end of the endoscope; a probe attached to the housing and having a wall with an outer surface and an inner surface;

one of the inner surface and the outer surface being non-circular in radial cross-section; and the outer surface being tapered.

21. The endoscope recited in claim 20 wherein the non-circular surface and the tapered surface are the same surface.

22. The endoscope recited in claim 20 wherein the non-circular surface and the tapered surface are different surfaces.

23. An endoscope having an axis extending between a proximal end and a distal end, comprising:

a housing disposed at the proximal end of the endoscope;

a probe attached to the housing and having a wall with an inner surface and an outer surface;

one of the inner surface and the outer surface having a configuration in a radial cross-section which is non-circular;

the other of the inner surface and the outer surface having a configuration in radial cross-section which is different than the configuration of the one surface; and the outer surface being tapered along the axis of the endoscope.

24. The rigid endoscope recited in claim 23 wherein the one surface has a configuration in radial cross-section which is oval.

* * * * *

UNITED STATES PATENT AND TRADEMARK OFFICE
CERTIFICATE OF CORRECTION

PATENT NO. : 5,213,093
DATED : May 25, 1993
INVENTOR(S) : Carl A. Swindle

It is certified that error appears in the above—identified patent and that said Letters Patent is hereby corrected as shown below:

Col. 2, line 26, after the word "an" delete the words "15".

Col. 5, line 40, change "5" to --51--.

Col. 6, line 38, change "6" to --65--.

Col. 7, line 13, after the word "the" delete "15"

Signed and Sealed this

Twenty-third Day of August, 1994

Attest:

BRUCE LEHMAN

Attesting Officer     Commissioner of Patents and Trademarks